(12) United States Patent
Bluecher et al.

(10) Patent No.: US 10,034,956 B2
(45) Date of Patent: Jul. 31, 2018

(54) CLASS OF ANTI-ADHESION HYDROGELS WITH HEALING ASPECTS

(71) Applicant: BVW Holding AG, Cham (CH)

(72) Inventors: Lukas Bluecher, Eurasburg (DE); Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 0 days.

(21) Appl. No.: 15/283,374

(22) Filed: Oct. 1, 2016

(65) Prior Publication Data

US 2017/0021053 A1     Jan. 26, 2017

Related U.S. Application Data

(63) Continuation of application No. 13/745,454, filed on Jan. 18, 2013, now Pat. No. 9,480,747.

(Continued)

(51) Int. Cl.
*A61L 26/00* (2006.01)
*A61K 47/32* (2006.01)
(Continued)

(52) U.S. Cl.
CPC ............ *A61L 26/0019* (2013.01); *A61K 9/06* (2013.01); *A61K 36/324* (2013.01); *A61K 47/32* (2013.01); *A61L 26/008* (2013.01); *A61L 26/009* (2013.01); *A61L 26/0023* (2013.01); *A61L 26/0066* (2013.01); *A61L 27/18* (2013.01); *A61L 27/52* (2013.01); *A61L 27/54* (2013.01); *C08G 18/10* (2013.01); *C08G 18/12* (2013.01); *C08G 18/244* (2013.01); *C08G 18/246* (2013.01); *C08G 18/2825* (2013.01); *C08G 18/3206* (2013.01); *C08G 18/4018* (2013.01); *C08G 18/428* (2013.01); *C08G 18/4277* (2013.01); *C08G 18/44* (2013.01); *C08G 18/48* (2013.01); *C08G 18/4825* (2013.01); *C08G 18/4833* (2013.01); *C08G 18/4837* (2013.01); *C08G 18/4854* (2013.01); *C08G 18/4887* (2013.01); *C08G 18/6484* (2013.01); *C08G 18/65* (2013.01); *C08G 18/73* (2013.01); *C08G 18/755* (2013.01);

(Continued)

(58) Field of Classification Search
None
See application file for complete search history.

(56) References Cited

U.S. PATENT DOCUMENTS 8,008,476 B2 * 8/2011 Moya .................. C08J 3/09
536/112

* cited by examiner

*Primary Examiner* — Robert A Wax
*Assistant Examiner* — Melissa S Mercier
(74) *Attorney, Agent, or Firm* — Patterson Intellectual Property Law, P.C.; Hilary Dorr Lang

(57) ABSTRACT

Disclosed are hydrogels polymerized with a biofunctional moiety, biodegradable and permanent, designed to be implantable in a mammalian body and intended to block or mitigate the formation of tissue adhesions. The hydrogels of the present invention are characterized by comprising four structural elements: a) a polymeric backbone which defines the overall polymeric morphology, b) linkage groups, c) side chains, and d) biofunctional end groups. The hydrophobicity of the various structural elements are chosen to reduce tissue adhesion and enhance the biofunctional aspect of the end groups. The morphology of these polymers are typically of high molecular weight and have shape to encourage entanglement. Useful structures include branching chains, comb or brush, and dendritic morphologies.

7 Claims, 2 Drawing Sheets

Related U.S. Application Data

(60) Provisional application No. 61/589,921, filed on Jan. 24, 2012.

(51) Int. Cl.
  *C08G 18/48* (2006.01)
  *C08G 18/64* (2006.01)
  *C08G 18/73* (2006.01)
  *C08G 18/75* (2006.01)
  *C08G 18/76* (2006.01)
  *C08G 18/10* (2006.01)
  *C08G 18/12* (2006.01)
  *C08G 18/24* (2006.01)
  *C08G 18/28* (2006.01)
  *C08G 18/40* (2006.01)
  *C08G 18/42* (2006.01)
  *C08G 18/44* (2006.01)
  *A61L 27/18* (2006.01)
  *A61L 27/52* (2006.01)
  *A61L 27/54* (2006.01)
  *A61K 9/06* (2006.01)
  *A61K 36/324* (2006.01)
  *C08G 18/32* (2006.01)
  *C08G 18/65* (2006.01)
  *C08G 83/00* (2006.01)

(52) U.S. Cl.
  CPC ....... *C08G 18/7621* (2013.01); *C08G 83/003* (2013.01); *A61L 2300/30* (2013.01); *A61L 2300/412* (2013.01); *A61L 2300/604* (2013.01); *A61L 2430/34* (2013.01); *C08G 2210/00* (2013.01); *C08G 2230/00* (2013.01)

CLASS OF ANTI-ADHESION HYDROGELS WITH HEALING ASPECTS

RELATED APPLICATION

This application claims the benefit of priority to U.S. Provisional Application No. 61/589,921, filed on Jan. 24, 2012, the contents of which are hereby incorporated by reference in their entirety.

TECHNICAL FIELD

The present disclosure relates to absorbable or biodegradable polymeric hydrogels and their biomedical and pharmaceutical applications, including wound healing and surgical applications. More particularly, the present disclosure provides hydrogel-forming, self-solvating, absorbable polymers that are capable of selective segmental association into compliant hydrogels upon contact with an aqueous environment.

BACKGROUND

A wound or may be accidental, the result of surgical intervention or the effect of a disease or genetic condition. The ideal end result of wound healing is restoration of tissues morphology. One important part of the wound healing process is to form connective tissues or scar tissue that may support the healing tissues during wound healing and regeneration. However, in many cases during wound healing, the newly formed connective tissues (scar tissue) may interfere negatively with the normal function of the tissue intended to be healed.

Wound healing, with the formation of connective tissues may also induce adhesions that may induce pathological conditions. For example, scar tissue may induce cosmetically undesirable results such as cheloid formation. Examples of adhesions and scarring may be found virtually in any organ or tissue undergoing wound healing after trauma or surgery. Following abdominal surgery and following gynecological surgery it is not uncommon that the surgical procedure may induce adhesions that may both make later surgery more difficult and even induce pathological conditions such as ileus.

In spinal surgery it is common to have a situation with a dense scar formation called epidural fibrosis. This may in certain cases induce significant difficulties for repeated surgery and can induce compression of the adjacent nerve tissue. In other organs excessive wound healing may induce unwanted fixation of tissues and structures that may reduce function and induce pathological conditions.

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection.

In intra-organ systems, tissue damage occurs that elicits an adhesion mechanism that results in migration or activation of leukocytes that can be damaging. For example, the initial insult following myocardial ischemia to heart tissue is complicated by leukocyte entry to the injured tissue causing still further insult. Inflammatory conditions mediated by adhesion mechanisms are almost always deleterious, for example, asthma, Alzheimer's disease, atherosclerosis, AIDS dementia, diabetes, inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Hydrogels have the potential to be useful in healing. However, one difficulty associated with in situ hydrogel forming compositions is that certain compositions may worsen tissue inflammation at the site of administration. A possible explanation for this effect is that highly reactive composition components that are capable of rapid gel formation may adversely affect tissue surfaces.

Therefore, it would be useful to develop a hydrogel which combines a barrier aspect with a biofunctional aspect which affects cellular adhesion and prevents clinically adverse tissue adhesions.

BRIEF SUMMARY

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

The present disclosure generally provides compositions and methods for treating tissue defects, wounds, or surgical sites, and modulating cell to cell interactions with a polymeric gel material containing bioactive molecules to a tissue surface.

In one embodiment, the present disclosure provides a copolymeric hydrogel comprising the polymerization product of a polymer comprising: a) aliphatic ester units, b) a polyethylene oxide, a polypropylene oxide, or both, c) a diisocyanate, and d) a chain extender or cross linker, wherein the hydrogel comprises at least 30% water by weight bound to the hydrogel by hydrogen bonding.

In another embodiment, the disclosure provides a copolymeric hydrogel comprising a polymerization product of an anionic polysaccharide, a diisocyanate, and a linker, wherein the linker comprises i) an ether group, an ester group, or a combination thereof and, ii) a chain extender comprising a hydroxyl group, a thiol group, an amine group, or a combination thereof, and wherein the hydrogel comprises at least 30% by weight of water bound by hydrogen bonding.

The disclosure further provides, in other embodiments, a copolymeric hydrogel comprising ester blocks and ether blocks, wherein the ester blocks have a negative free energy transfer and the ether blocks have a positive free energy transfer when in an aqueous environment, wherein the ether and ester blocks are less than $\frac{1}{10}$ the length of said copolymer, wherein the ether and ester blocks are distributed such that no domain of contiguous blocks have the same polarity of free energy transfer are less than $\frac{1}{3}$ of the molecular weight of the copolymer, and wherein the copolymeric hydrogel comprises at least 30% by weight of water bound to the hydrogel by hydrogen bonds.

Alternatively, the disclosure provides, a copolymeric hydrogel for implantation comprising polysaccharide blocks and ether blocks, wherein the polysaccharide blocks have a negative free energy transfer and the ether blocks have a positive free energy transfer in an aqueous environment, wherein the polysaccharide and ether blocks are less than 1/10 the length of said copolymer, wherein and the polysaccharide and ether blocks are distributed such that no domain of contiguous blocks have the same polarity of free energy transfer are less than 1/3 of the molecular weight of the copolymer, and wherein the copolymeric hydrogel comprises at least 30% by weight of water bound to the hydrogel by hydrogen bonds.

In yet another embodiment, the disclosure provides a copolymeric hydrogel comprising polysaccharide blocks and ester blocks, wherein the ester blocks have a negative free energy transfer and the polysaccharide blocks have a positive free energy transfer in an aqueous environment, wherein the blocks are less than 1/10 the length of said copolymer, and polysaccharide blocks and ester blocks are distributed such that no domain of contiguous blocks having the same polarity of free energy transfer are less than 1/3 of the molecular weight of the copolymer, and wherein the copolymeric hydrogel comprises at least 30% by weight of water bound to the hydrogel by hydrogen bonds.

In particular embodiments, the present invention relates to hydrogel-forming, self-solvating, absorbable polymers capable of selective, segmental association into compliant hydrogels upon contacting an aqueous environment.

The disclosure also provides methods of using the hydrogel copolymers in humans, for example to provide a protective barrier to prevent post-surgical adhesion, a carrier of viable cells or living tissue, treatment of defects of the abdomen, and controlled release of biologically functional molecules for modulating cellular signaling such as wound healing and tissue regeneration or therapeutic treatment of diseases such as cancer and infection.

Other embodiments provide copolymers that contain polysaccharide chains or polyester chains, particularly alginate or modified alginate chains, but includes modified cellulose, hyaluronate, polylactic acid, polyurethane, and ethylene or propylene moieties.

The polysaccharide, particularly alginate or modified alginate, chains may be included as side chains or auxiliary chains from a backbone polymer chain. The backbone is typically an ether, containing polyethylene oxide or polypropylene oxide. In other embodiments, the backbone may also be a polysaccharide, such as alginate associated with cellulose.

Further, the polysaccharide chains may be crosslinked between side chains, auxiliary chains and/or backbone chains. These materials are advantageously modified by covalent bonding thereto of biologically active molecules for cell adhesion signaling or other cellular messaging.

This invention relates also to derivatized carboxypolysaccharides (CPS). Specifically, this invention relates to derivatized carboxypolysaccharides and uses in manufacturing gels and films incorporating polyethylene oxide (PEO) or polypropylene oxide (PPO) for drug delivery and for anti-adhesion preparations. More specifically, this invention relates to anti-adhesion and healing compositions comprising composites of biofunctionalized CPS, PEO and PPO.

One embodiment of the invention is directed to polymers containing a polymer backbone to which is linked polysaccharide groups, particularly alginates or modified alginates, which preferably are polymerized D-mannuronate and/or L-guluronate monomers. The polysaccharide, particularly alginate, groups are present as side chains on the polymer backbone which is intended to include side chains at the terminal end of the backbone, thus being a continuation of the main chain.

The polymers may include synthetically modified polysaccharides and alginates exhibiting controllable mechanical and charge distribution properties to which an organic moiety may be attached.

Further, the invention is directed the use of such polymers, for example, as cell transplantation matrices, preformed hydrogels for cell transplantation, non-degradable matrices for immunoisolated cell transplantation, vehicles for drug delivery, wound dressings and anti-adhesion prosthetics.

Another embodiment of the invention is directed to polysaccharides, particularly alginates, which are modified by being crosslinked with an organic biofunctional molecule. The alginates may further be modified by covalent bonding thereto a biofunctional molecule for cell adhesion or other cellular interaction. Crosslinking of the alginate can particularly provide alginate materials with controlled mechanical properties and shape memory properties which greatly expand their range of use.

In many applications, such as tissue engineering, size and shape of the matrix is of importance. Modification of crosslinked alginates with the biologically active molecules can provide a further three-dimensional environment. This is particularly advantageous for mitigation of tissue adhesion on a first untreated side (by degradation of the outer layers) while promoting tissue ingrowth on a second treated side. The second side may have a longer persistence than the first side.

Another embodiment of the invention is directed to modified alginates, such as polymers containing an alginate backbone or the above described side chain alginates or crosslinked alginates, modified by covalent bonding thereto of a biologically active molecule for mitigation of cell adhesion or other cellular interaction, which is particularly advantageous for maintenance, viability and directed expression of desirable patterns of gene expression. For example, a terminal group that stimulates nitric oxide production, and thus promoted angiogenesis. Alternatively, a terminal groups that comprises a constituent of a botanical extract with healing or anti-aging properties.

In particular, the biofunctional molecules include those obtained from various extracts and purification of *Boswellia* genus botanicals. More particularly, the extracts have a polycyclic structure with one or more pendant hydroxyl groups, such as cyclic terpene compounds. These biofunctional molecules are covalently bonded, using the hydroxyl group, to join a polymeric backbone or side chain to the biofunctional molecules. Preferably, the biofunctional molecule is chiral. The chirality can be due to an odd number of cyclic structures, or a asymmetric terminal chain. The biofunctional molecules may include, in certain embodiments, synthetic analogous of naturally occurring structures.

The present compositions may be advantageously used, for example, in the reduction or prevention of adhesion formation subsequent to medical procedures and as lubricants and sealants. In addition, the present compositions may be used as coatings and transient barriers in the body, for materials which control the release of bioactive agents in the body (drug delivery), for wound and burn dressings and for producing biodegradable and non-biodegradable articles, for example.

Yet another object of the present invention is to provide a gel polymer optionally terminated with a biologically active agent. A further object of the present invention, is to provide a gel polymer capable of the controlled-release or presentation at an implant surface of a biologically active agent/drug for modulating cellular events, such as, wound healing and tissue regeneration.

A further object of the present invention, is to provide a gel polymer capable of the controlled-release or presentation at an implant surface of a biologically active agent/drug for therapeutic treatment of diseases.

A further object of the present invention, is to provide a gel polymer which is capable of being extruded onto or injected into living tissue for providing a protective barrier with or without an anti-inflammatory agent or an agent, which inhibits fibrotic tissue production, such as, post-surgical adhesions.

A further object of the present invention, is to provide a gel polymer which is capable of being extruded onto or injected into living tissue for providing a protective barrier with or without a wound healing agent or an agent which promotes vascularization, for example in soft tissue repair.

A further object of this invention is to provide a gel polymer for delivering a botanical extract possessing anti-inflammatory or wound healing properties, for example extracts derived from the genus *Boswellia*.

A further object of the present invention is to provide a gel polymer which is capable of acting as a blocking agent or sealant for treating surgically modified tissue.

DETAILED DESCRIPTION

Figure 1:
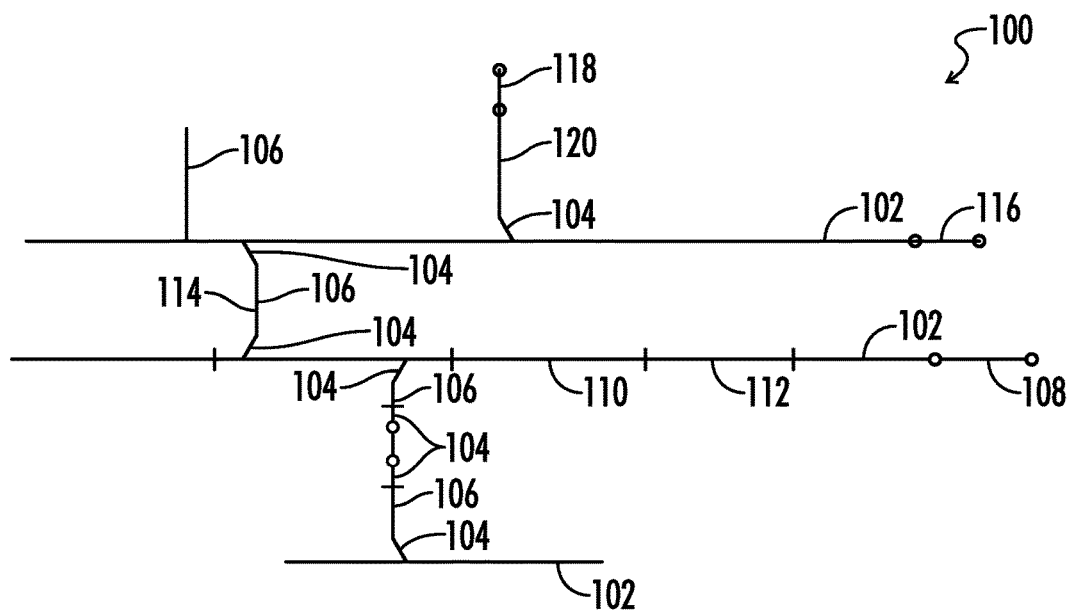
FIG. 1 Depicts a schematic of a gel polymer of the present disclosure.

Reference now will be made in detail to the embodiments of the present disclosure, one or more examples of which are set forth herein below. Each example is provided by way of explanation of the embodiments of the present disclosure and is not a limitation. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

The present disclosure provides a copolymeric hydrogel comprising the polymerization product of a polymer comprising: a) aliphatic ester units, b) a polyethylene oxide, a polypropylene oxide, or both, c) a diisocyanate, and d) a chain extender or cross linker, wherein the polymerization product comprises at least 30% water by weight bound to the hydrogel by hydrogen bonding.

For example, in some embodiments, the polymerization product comprises at least one segment represented by $\{\{D_r[A_n(B_p)A_n]D_r\}E\}_m$, wherein independently for each occurrence, A represents an aliphatic ester unit, B represents an ethylene oxide group, D is the diisocyanate, m is an integer greater than or equal to 2, n is an integer ranging from 20 to 50, p is an integer greater than or equal to 1, and r is an integer greater than or equal to 1.

In some embodiments, the copolymeric hydrogel of claim 1, wherein the aliphatic ester is an a polylactic lactic acid, a polycarbonate, a polycaprolactone, a polypropylene carbonate, or a combination thereof.

The polymeric hydrogel may comprise a biofunctional molecule. For example, the polymerization product comprises in certain embodiments, at least one segment represented by $\{\{D_r[A_n(FB_pC_qB_pF)A_n]D_r\}E\}_m$, wherein independently for each occurrence, A represents an aliphatic ester unit, B represents an ethylene oxide group, C represents a propylene oxide group, D is the diisocyanate, and F is the biofunctional molecule, m is an integer greater than or equal to 2, n is an integer ranging from 20 to 50, p is an integer greater than or equal to 1, q is an integer greater than 1, and r is an integer greater than or equal to 1.

In yet another embodiment, the copolymeric hydrogel of claim 5, wherein the polymerization product comprises at least one segment represented by $\{\{D_r[A_n(FB_pDC_qDB_pF)A_n]D_r\}E\}_m$, wherein independently for each occurrence, A represents an aliphatic ester unit, B represents an ethylene oxide group, C represents a propylene oxide group, D is the diisocyanate, and F is the biofunctional molecule, m is an integer greater than or equal to 2, n is an integer ranging from about 20 to about 50, p is an integer greater than or equal to 1, q is an integer greater than 1 and r is an integer greater than or equal to 1.

In still a further embodiment, the copolymeric hydrogel comprises at least one segment represented by $\{\{D_r[A_n(FB_pF)A_n]D_r\}E\}_m$, wherein independently for each occurrence, A represents an aliphatic ester unit, B represents an ethylene oxide group, D is the diisocyanate, F is the biofunctional molecule, m is an integer greater than or equal to 2, n is an integer ranging from 20 to 50, p is an integer greater than or equal to 1, and r is an integer greater than or equal to 1.

In any of the aforementioned segment formulas, m, n, p, q, and r can independently be as follows: m is an integer greater than or equal to 2 (for example, about 2 to about 50), n is an integer ranging from about 20 to about 50, p is an integer greater than or equal to 1 (for example, from about 1 to about 10,000, about 1 to about 5000, about 1 to about 2000, about 1 to about 1000, about 1 to about 500, about 1 to about 250 or about 1 to about 100; alternatively, about 100 to about 10,000, about 100 to about 5000, about 200 to about 5000, or about 100 to about 500), q is an integer greater than 1 (for example, from about 1 to about 10,000, about 1 to about 5000, about 1 to about 2000, about 1 to about 1000, about 1 to about 500, about 1 to about 250 or about 1 to about 100; alternatively, about 100 to about 10,000, about 100 to about 5000, about 200 to about 5000, or about 100 to about 500), and r is an integer greater than or equal to 1 (for example, from about 1 to about 10,000, about 1 to about 5000, about 1 to about 2000, about 1 to about 1000, about 1 to about 500, about 1 to about 250 or about 1 to about 100; alternatively, about 100 to about 10,000, about 100 to about 5000, about 200 to about 5000, or about 100 to about 500).

In certain embodiments, the aliphatic ester is a polylactic lactic acid, a polycarbonate, a polycaprolactone, a polypropylene carbonate. Further materials useful in the aforementioned gels are described in detail below.

Another embodiment provides a copolymeric hydrogel comprising a polymerization product of an anionic polysaccharide, a diisocyanate, and a linker, wherein the linker comprises i) an ether group, an ester group, or a combination thereof and, ii) a chain extender comprising a hydroxyl group, a thiol group, an amine group, or a combination thereof, and wherein the copolymeric hydrogel comprises at least 30% by weight of water bound to the hydrogel by hydrogen bonding. In certain embodiments, the polymerization product comprises a copolymer of a prepolymer and the linker, wherein: the prepolymer comprises a copolymer of the anionic polysaccharide and the diisocyanate. More particularly, the prepolymer comprises, in certain embodiments, at least one segment represented by I[UPUUPU]sI, wherein, independently for each occurrence, P represents a polysaccharide block, U represents a urethane or urea block, I represents an isocyanate and s represents and integer ranging from 1 to 10,000.

In certain embodiments, the linker comprises at least one segment represented by EGE, wherein, independently for each occurrence, G represents an ether block, an ester block or a combination thereof, and E represents a chain extender comprising a hydroxyl, a thiol or an amine group.

In other embodiments, wherein the polymerization product comprises at least one segment represented by I[UPUUPU]$_s$UGU[UPUUPU]$_s$I, wherein, independently for each occurrence, P represents a polysaccharide block, U represents a urea or urethane block, G represents an ether block, an ester block or a combination thereof, and s represents an integer ranging from 1 to 10,000. In other embodiments, s is independently for each occurrence, an integer greater than or equal to 1 (for example, from about 1 to about 10,000, about 1 to about 5000, about 1 to about 2000, about 1 to about 1000, about 1 to about 500, about 1 to about 250 or about 1 to about 100; alternatively, about 100 to about 10,000, about 100 to about 5000, about 200 to about 5000, or about 100 to about 500), q is an integer greater than 1 (for example, from about 1 to about 10,000, about 1 to about 5000, about 1 to about 2000, about 1 to about 1000, about 1 to about 500, about 1 to about 250 or about 1 to about 100; alternatively, about 100 to about 10,000, about 100 to about 5000, about 200 to about 5000, or about 100 to about 500), and r is an integer greater than or equal to 1 (for example, from about 1 to about 10,000, about 1 to about 5000, about 1 to about 2000, about 1 to about 1000, about 1 to about 500, about 1 to about 250 or about 1 to about 100; alternatively, about 100 to about 10,000, about 100 to about 5000, about 200 to about 5000, or about 100 to about 500).

Diisocyanates useful in the present disclosure include aliphatic or aromatic diisocyanates, including but not limited to toluene diisocyanate and isophorone diisocyanate. Additional diisocyanates useful in the present polymers are described below.

In another embodiment, the present disclosure provides a copolymeric hydrogel comprising ester blocks and ether blocks, wherein the ester blocks have a negative free energy transfer and the ether blocks have a positive free energy transfer when in an aqueous environment, wherein the ether and ester blocks are less than 1/10 the length of said copolymer, wherein the ether and ester blocks are distributed such that no domain of contiguous blocks have the same polarity of free energy transfer are less than 1/3 of the molecular weight of the copolymer, and wherein the copolymeric hydrogel comprises at least 30% by weight of water bound to the hydrogel by hydrogen bonds.

Alternatively, a copolymeric hydrogel for implantation comprises polysaccharide blocks and ether blocks, wherein the polysaccharide blocks have a negative free energy transfer and the ether blocks have a positive free energy transfer in an aqueous environment, wherein the polysaccharide and ether blocks are less than 1/10 the length of said copolymer, wherein and the polysaccharide and ether blocks are distributed such that no domain of contiguous blocks have the same polarity of free energy transfer are less than 1/3 of the molecular weight of the copolymer, and wherein the copolymeric hydrogel comprises at least 30% by weight of water bound to the hydrogel by hydrogen bonds.

In yet another embodiment, a copolymeric hydrogel comprising polysaccharide blocks and ester blocks, wherein the ester blocks have a negative free energy transfer and the polysaccharide blocks have a positive free energy transfer in an aqueous environment, wherein the blocks are less than 1/10 the length of said copolymer, and polysaccharide blocks and ester blocks are distributed such that no domain of contiguous blocks having the same polarity of free energy transfer are less than 1/3 of the molecular weight of the copolymer, and wherein the copolymeric hydrogel comprises at least 30% by weight of water bound to the hydrogel by hydrogen bonds.

Polysaccharides useful in the aforementioned hydrogels include alginates, hyaluronic acid, and carboxypolysacharides. Additional polysaccharides useful in these embodiments, are described in detail herein below.

The aforementioned hydrogels comprise a biofunctional molecule, in certain embodiments. For example, the biofuncational molecule may be obtained from a *Boswellia* extract. Such compounds include terpenes, and more particularly cyclic terpenes having at least one hydroxyl group. In other embodiments, the hydrogels comprise a *Boswellia* extract fraction.

The aforementioned hydrogels may advantageously comprise the copolymer has a dendritic or comb backbone.

The hydrogels comprise at least 30%, at least 40% by eight of water, o at least 50% by weight of water. In other embodiments, the hydrogels comprise 30% by weight to 99.9%, 30% to 80%, 30% to 70% or 30% to 50% by weight of water.

Complex carbohydrates, useful in the aforementioned polymeric hydrogels include polysaccharides and oligosaccharides. Polysaccharides include mucopolysaccharides and mannans whereas oligosaccharides are comprised of branched polysaccharides such as sialylated sugars including milk sugars.

Mucopolysaccharides are glycosaminoglycans can be obtained from numerous sources (e.g. rooster combs, trachea, umbilical cords, skin, articular fluids and certain bacteria such as Streptococci). Most glycosaminoglycans (hyaluronic acid, chondroitin sulfates A, B, and C, heparin sulfate, heparin, keratan sulfate, dermatan sulfate, etc.) comprise repeating sugars such as n-acetylglucosamine, glucuronic acid and n-acetyl galactosamine. If such glycosaminoglycans contain sulfur groups they are known as sulfated glycosaminoglycans. All of these can be combined with other polysaccharides or with alkane groups.

On the other hand, for tissue healing applications, it is desirable that the polymeric material used forms a biodegradable scaffold for cells, promote cell adhesion, migration, growth and differentiation while providing adequate structural support; and without promoting an inflammatory response.

In some embodiments, an anti-adhesive surface for many biomaterials applications, such as the applications of the present disclosure, would resist protein adsorption while providing molecules with specific chemical signals to guide adhesion, survival, growth, migration and differentiation in a tissue defect.

As used herein, the term "biomaterial" refers to a material used in a medical device intended to interact with a biological system. For example, a typical biomaterial is modified with polyethylene oxide. The objective of these surface modification schemes is the elimination of nonspecific interactions of cells with implant materials. Polyethers can be combined with hydrophobic biomaterials to shield the hydrophobic biomaterials from the foreign body response, and thus provide them to the body directly rather than through a fibrotic capsule.

Activation-specific chemical signals can be relayed to cells at a surface through tethered ligands of cell surface receptors. These signals are presented in a localized manner at a controlled dose without diffusive loss. The mimicry of tethered ligands through the addition of bioactive moieties may provide more constant stimulation to cells by avoiding the down-regulation present when soluble ligands are internalized by cells. Control over spatial distribution of ligands on surfaces may also be key to guiding cell behavior. Thus, systems which allow spatial control of local ligand density, or clusters of ligands on a surface, in addition to providing control over the average surface density of ligands, are highly desirable. In the present invention these ligands are associated with a biofunctional moiety.

Additionally, molecules with dimeric adhesion receptors are particularly useful as ligands and include approximately ten known alpha chains paired with one of approximately six known beta chains, which are known to mediate a wide range of interactions between cells and extracellular matrix and control cell behaviors as diverse as migration, growth, and differentiation, providing a permissive environment for the action of growth factors. Thus, such molecules are particularly useful in facilitating a healing response.

An important aspect of healing involves cross-communication between adhesion and growth factor receptors, and it is hypothesized that these factors work competitively in wound healing. Therefore, favoring growth factor expression over adhesion formation, would be advantageous. Therefore, a biofunctional molecule delivered in close proximity to adhesion and growth factor receptors in the focal healing complex can modulate the flow of signals between the two.

In particular, a hierarchical hydrophobic-hydrophilic domain structured polymer endcapped with a biofunctional molecule can beneficially undergo morphological changes which are associated with the hydration of the hydrophilic domains and formation of pseudo-crosslinks via the hydrophobic component of the system. Such polymeric structures form biocompatible gels in vivo with extended persistence by virtue of the pseudo-crosslinks.

Hydrophobic-hydrophilic polymer morphology can be affected by temperature and pH, especially for extended and hydrated systems, and is responsible for thermoreversible gels. In order for these gels to maintain their short-term structure in vivo, regardless of their longer-term biodegradability, involves covalent bonds between water-soluble and water-insoluble blocks.

In the case where the hydrophilic blocks and hydrophobic blocks are a mixture or blend and not polymerized together, the desired structural aspects are not achieved since the hydrophilic component rapidly disperses in tissue. Polymers comprised of covalently bonded hydrophilic and hydrophobic domains exhibit a hydration-dehydration equilibrium which can be altered by changes in temperature or pH. The equilibrium structures are characteristic of hydrogels.

Thus, hydrogels in the absence of hydrophobic-hydrophilic covalent bonding, the hydrophilic blocks undergo intermolecular segmental mixing with the neighboring hydrophobic blocks to produce a viscous liquid. With hydrophobic-hydrophilic covalent bonding, competition between the water and the hydrophilic block forces hydration of the hydrophobic block, and results in an association of the hydrophobic blocks to form pseudo-crosslinks which have 3-dimensional integrity.

The mechanism of gel formation in vivo is associated with orientation of the hydrophobic block toward the exterior of the gel and the interface with the adjoining tissues can be used to establish an adhesive joint, which prevents gel migration from a target site. Additionally, this effect can be enhanced by the endcapping of a biofunctional moiety, which is relatively more hydrophobic than the remaining portion of a polymeric chain of hydrophobic and hydrophilic blocks. Thus, the biofunctional moiety is presented at the surface of the hydrogel and is predisposed to block tissue adhesions.

Chemical bonding can be carried out by a chemical reaction, e.g. gelation with a polyfunctional reagent; crosslinking using a coordinate bond, e.g. gelation by calcium ions of alginic acid; crosslinking using a hydrophobic bond, e.g. gelation by heating methyl cellulose or hydroxypropyl cellulose; crosslinking using intermolecular association, e.g. cooling of agar or carrageenan to cause the gelation, or the like. The density of crosslinking can impact water absorbability and strength of the resulting gel as well as rate of degradation in vivo.

However, hydrogels can be formed without the use of crosslinking at all, and which rely on entanglement. Entanglement and the formation of pseudo-bonds between hydrophobic segments requires the hydrophobic and hydrophilic segments to be covalently bonded together in long structures. The covalent bonding prevents the separation of the hydrophobic and hydrophilic components.

The chemical structures and methods of the present invention concern gels, more particularly hydrogels, comprised of hydrophilic blocks, hydrophobic blocks and a biofunctional moiety. The hydrogels of the present invention are intended for implantation in a mammalian body and may be absorbable or alternatively relatively persistent.

The hydrophobic blocks may be absorbable polyester chain blocks, polyoxypropylene blocks, urethane segments and botanical extract molecules. Of particular interest are cyclic lactones, for example glycolide, l-lactide, dl-lactide, .epsilon.-caprolactone, and p dioxanone. With respect to botanical extracts, polycyclic structures are of particular interest, for example boswellic acid derived from *Boswellia*. Examples include, boswellic acids, tirucalic acids, thujenes, champhenes, and the like, or their synthetic analogs.

The hydrophilic blocks may be polyoxyethylene blocks, polysaccharides, or derivatives thereof. The length of the hydrophilic block and its weight fractions can be varied to modulate the rate of gel formation, its modulus, its water content, diffusivity of bioactive drug through it, its adhesiveness to surrounding tissue, and bioabsorbability.

The polymers constructed from these constituents are typically long chains with multiple pendant end groups, commonly referred to as comb- or brush-type copolymers that elicit controlled cellular response.

The backbone or chain portion of the polymer can be biodegradable or non-biodegradable, depending on the intended application. Biodegradable backbones are preferred for most tissue engineering, drug delivery and wound healing device applications, while non-biodegradable backbones are desirable for permanent implant applications.

A portion of the side chains can be end-capped with cell-signaling polycyclic structures functionalized with ligands to control the degree of cell adhesion and tissue healing. The cell-signaling can be elicited at the polymer surface or released into the surrounding tissue through degradation of a portion of the polymer.

In one embodiment, the overall comb copolymer should have a molecular weight sufficiently high as to confer good mechanical properties to the polymer in the hydrated state through chain entanglement. That is, its molecular weight should be above the entanglement molecular weight, as defined by one of ordinary skill in the art. The overall molecular weight of the comb copolymer should thus be above about 30,000 Daltons, more preferably above 100,000 Daltons, and more preferably still above 1 million Daltons.

The side chains are preferably hydrophilic and degradable, and the polymer backbone contains a multiplicity of hydrophilic, degradable blocks. The density of the hydrophilic side chains along the backbone of the polymers depends on the length of the side chains and the water-solubility characteristics of the final polymer. The total percentage by weight of the hydrophilic side chains is between 10 and 50 percent of the total copolymer composition, preferably around 30 percent by weight. Preferably, the hydrophilic side chains associate with water and form a hydrated layer which repels proteins and hence resists cellular adhesion.

The side chains of the comb polymer can be end-capped with cell-signaling molecules modified by chemical ligands in order to elicit controlled cell responses. Ligands capable of bonding to hydroxyl groups, for example diisocyanates, can be covalently attached to the hydroxyls of biofunctional molecules and in turn attached to the hydroxyl groups of the polymer side chains.

A defined fraction of biofunctionalized side chains can be obtained by using appropriate stoichiometric control during the coupling of the ligands to the polymers, by protecting the end-groups on those side chains which are not to be end-capped with the biofunctional molecule, or by combinations of these approaches. Generally, the ligands are attached to the biofunctional molecule first, which then enables the biofunctional molecules to link to the polymer side chains without leaving exposed ligands which may promote protein attachment and subsequently adhesions.

In one embodiment, the invention provides a backbone of polyoxyethylene, polyoxypropylene, or combinations of these in chain form with multiple hydroxyl groups to which are covalently attached side chains of polysaccharides. It is not necessary that the polysaccharides exhibit the gelling behavior of alginates, since the backbone can alternatively form a hydrogel. In this case the main function of the polysaccharide would be to control the degradation rate and modification of the hydrophobicity of biofunctional end groups.

Another embodiment provides a polymeric backbone section to which is bonded a side chain, preferably multiple side chains, of polymerized, optionally modified, D-mannuronate and/or L-guluronate monomers. The modified alginates preferably maintain the mild gelling behavior of conventional alginates.

The linkage between the polymeric backbone section and the side chains may be provided by difunctional or multifunctional linker compounds, for example diisocyanates, or by groups incorporated within the polymeric backbone section reactive with the polysaccharide units or by groups on the polysaccharide units or derivatives thereof reactive with groups on the polymeric backbone section. The polymers may advantageously further comprise biologically active molecules bonded to the side chains, particularly preferably bonded through the hydroxyl groups on D-mannuronate and/or L-guluronate monomers.

In a particularly preferred embodiment, the side chains are alginates, the biologically active molecules exhibit cell anti-adhesion properties and the polymers provide a mucoadhesivity for localizing the hydrogel in vivo without forming tissue adhesions.

In a yet more preferred embodiment, the side chains are alginates, the biologically active molecules are of two types, some of which exhibit cell anti-adhesion properties and others exhibit angiogenic properties, and the polymers provide a mucoadhesivity for localizing the hydrogel in vivo to repair a wound site and protect the healing wound site from tissue adhesions.

When a linker group or ligand is used, such linker groups may be selected from any divalent moieties which are compatible with the ultimate use of the polymer and which provide for covalent bonding between the polymeric backbone section and the polysaccharide side chains and additionally any biofunctional end groups.

When polysaccharides are used, it is conventional for the polysaccharide to be bonded through a carboxylate group. In this case, the linker group may be selected to significantly affect the biodegradability of the polymer depending upon the extent of hydrolyzability of groups in the linker chain. For example, amino acid linkers are frequently used due to the controllability of the degradation interval. For example, amino acid linker groups, such as glycine, will provide ester linkages which are readily hydrolyzable and, thus, facilitate degradation of the polymer in an aqueous environment, whereas, amino alcohols provide an ether linkage which is significantly less degradable. Amino aldehydes are also useful linker groups. The substituent groups on the amino acids will also affect the rate of degradability of the linkage.

The linker group may also be varied in chain length depending upon the desired properties. Linkages providing, for example, from 10 to 20 atoms between the backbone and side chain, are typical, although longer linkage chains are possible. Additionally, the linker may be branched to provide for clustering of multiple side chains. These structures are typically referred to as dendritic in structure because they may provide a multiplicity of branching points.

The polymeric backbone section, linkages, side chains and biofunctional end groups may be provided in a number of hydrophilic and hydrophobic configurations which will largely determine the stability of the resulting hydrogel. The polymeric backbone itself may be comprised of alternating hydrophobic and hydrophilic blocks. Since the biofunctional endgroups are typically hydrophobic, it is generally useful to modify their hydrophobicity by attaching them to hydrophilic side chains.

Examples of useful configurations are shown in FIG. 1 although the invention is not limited to such configurations and further configurations using the four basic structural units can be provided according to the invention. FIG. 1 depicts gel polymer 100 of the present invention comprising: a polymeric backbone 102 which defines the overall polymeric morphology, linkage groups 104, side chains 106, and biofunctional end groups 108. The backbone 102 is generally comprised of hydrophobic 110 and hydrophilic 112 group segments, some or all of which can be biodegradable. Linkage groups 104 form bridges 114 between the backbones 102, and may be of an entirely different composition than the backbone. Typically the bridges comprise linkage groups 104 and side chains 106, wherein the backbones 102 are joined to side chains 106 through linkage groups 104. The biofunctional group 108 may optionally be located on the ends 116 of the backbone 102, on the ends 118 of pendant side chains 120, sandwiched between a linkage group 104 and a biofunctional group 120 and a linkage group 104 which in turn links to a side chain 106. Biofunctional groups 122 may be located at the junction of two side chains 106 connected by linkage groups 104.

In one embodiment, the backbone itself is a polysaccharide, for example alginate. Side chains, for example, may be hyaluronan. A particular example involves chains of D-mannuronate and L-guluronate units to which are attached hyaluronan side chains functionalized with a diisocyanate linker.

Dendritic polymers and comb polymer backbones can be provided by the polymerization product of difunctional and higher functional prepolymers. For example linear chains of polysaccharide pendant hydroxyl groups can be polymerized with triol endcapped with isocyanate groups. These structures can provide a highly cross-linked polymer which would rapidly degrade to low molecular weight components and readily be cleared by the body.

Figure 2:
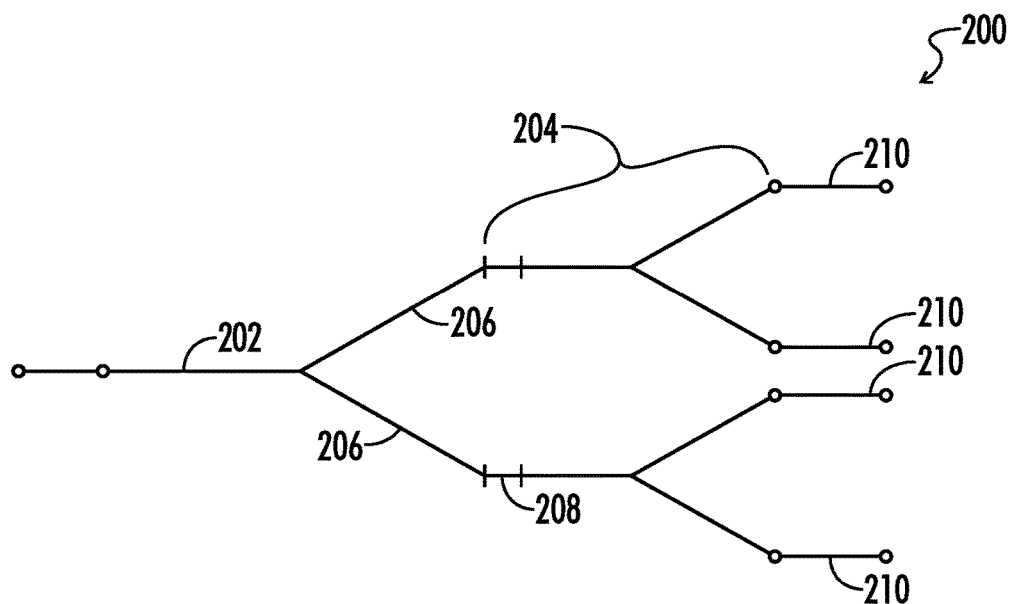
FIG. 2 depicts a bifurcating sequence of a gel polymer of the present disclosure.

For example, FIG. 2 illustrates a bifurcating sequence 200 wherein a polymer backbone 202 has a 3-armed structure 204 comprised of two side chains 206. The terminus of each 3-armed structure 204 is linked to another 3-armed structure 204 through linkage group 208. At the final terminus of the bifurcating structure are located pendant biofunctional groups 210.

When it is desirable that the entire hydrogel be alginate based, polyaldehyde guluronate can be reacted with hydrazine and sodium borohydride to yield polyhydrazino guluronate. The hydrazine groups on this alginate derived polymer are used to incorporate L-guluronate side chains at their hemiacetal termini. The resulting hydrolyzable hydrazone linkages are easily degraded in vivo yielding short chain polysaccharides that can be excreted by the kidney.

Alternatively, borohydrides can be used to convert the hydrazone bond to a hydrazine bond that provide non-degradable materials. Both biodegradable and non-degradable biomaterials can be derived from natural polysaccharides.

Figure 3:
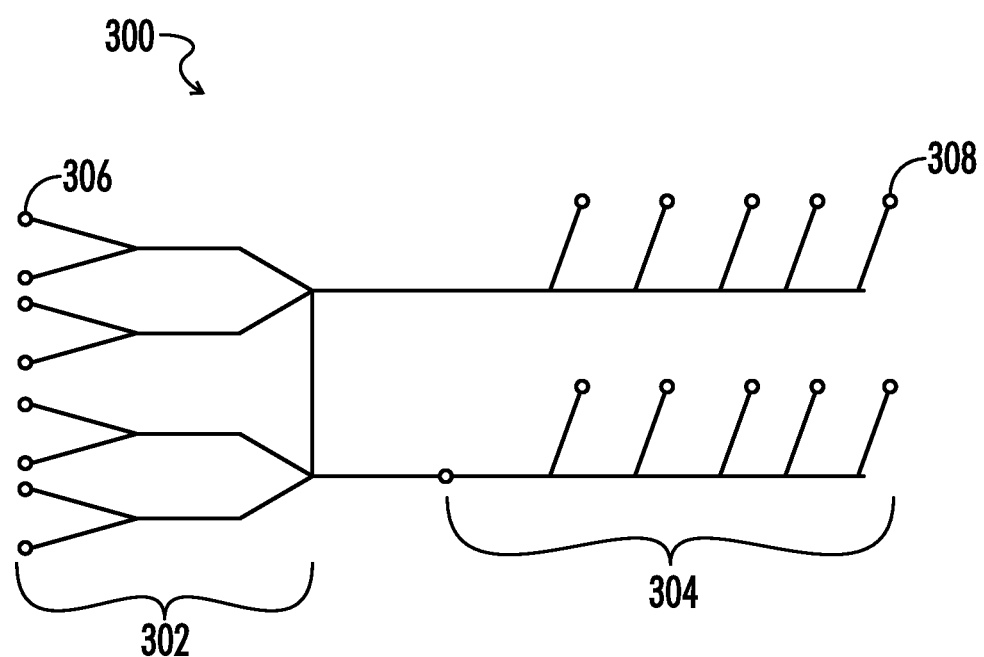
FIG. 3 Depicts dendritic and comb gel polymers of the present disclosure.

Dendrimers are of particular interest due to their propensity for entanglement and the formation of hydrogels that are relatively stable in the implant environment. Referring to FIG. 3, mixtures 300 of dendritic 302 and comb 304 polymers are possible wherein the dendritic portion serves as a scaffold to the more mobile comb structures. Therefore, the dendritic fraction may be principally endcapped with anti-adhesion end groups 306 and the comb fraction may be endcapped with angiogenic end groups 308. Alternatively, the comb fraction may be a hyaluronan based gel and the dendritic fraction an alginate based gel. Polymers containing hyaluronan are known to act as tissue scaffolds, mimicking their biological function in living extracellular matrix.

A further useful backbone structure is comb polymers which contain many side chains extending from a polymer backbone. Polyvinyl alcohol provides a particularly useful backbone for comb polymers. The alcohol groups of polyvinyl alcohol can be esterified and subjected to the a carbodiimide linkage chemistry to provide the side chain linkages.

The present invention provides hydrogel-forming, self-solvating, absorbable polymers endcapped with biofunctional end groups capable of selective, segmental association into a compliant hydrogel in an aqueous environment.

The polymers of the present invention are comprised of four structural elements: a) a polymeric backbone which defines the overall polymeric morphology, b) linkage groups, c) side chains, and d) biofunctional end groups.

Referring now to component (a), the polymeric backbone may possesses a comb or dendritic morphology comprised of hydrophobic and hydrophilic blocks. The hydrophobic blocks provide volume stability and resistance to degradations; and, the hydrophilic blocks associate water with the polymer. In forming gels with water content in excess of 50% by volume, the mass ratio between hydrophobic blocks and hydrophilic blocks may be 50:50, and more preferably 30:70. Depending on the constitution of the blocks, if some are hydrolysable, then higher hydrophilic content also correlates with increased degradation rate. In some instances it may be desirable to decouple the degradation properties from the hydrophobicity of the polymeric backbone. In this case, the hydrolyzable units are selected to be the component (b) elements, or the linkage groups.

The hydrolyzable block may be hydrophobic, for example a glycolide, lactide, .epsilon.-caprolactone, p-dioxanone, or combinations thereof. In general, polyesters are biodegradable. In this case, one might employ an ester of a carboxyl group-containing polysaccharide. For example, a compound formed by bonding at least one of the carboxyl groups of the carboxyl group-containing polysaccharide, preferably at least two of the carboxyl groups of the carboxyl group-containing polysaccharide, with hydroxyl groups of an alcohol to form ester bonds. Among the esterified polysaccharides, those substantially water-soluble are preferable.

The hydrolyzable group may be a polysaccharide, for instance, carboxyl group-containing polysaccharides, such as alginic acid, xanthane gum, gellan gum, derivatives of hyaluronan, and derivatives of polysaccharides which do not have carboxyl groups, such as carboxymethyl cellulose, carboxymethyl dextran and carboxymethyl pullulan; chitin or chitosan derivatives into which carboxyl groups are introduced, such as partially maleylated chitosan, partially succinylated chitosan, carboxymethyl chitosan and carboxymethyl chitin; and the like. Among the above, alginate and hyaluronan are preferable, from the viewpoint of safety and clinically relevant absorption rates.

These polymers are characterized by properties that are a function of the type and ratio of hydrophilic blocks to hydrophobic blocks or structure of mixed hydrophobic/hydrophilic backbone polymers, type and number of tethered cell-signaling end groups, molecular weight, crosslink density and polymeric morphology.

The polymers of the present invention are comb- or dendrite-type polymers, with a backbone formed of a hydrophobic, water-insoluble polymer relative to the side chains. Preferably, the side chains comprise short, hydrophilic non-cell binding polymers, with a molecular weight of between 100 and 10,000 Daltons.

The hydrophobic backbone can be biodegradable or non-biodegradable, depending on the desired application. The overall polymer morphology should have a molecular weight sufficiently high to confer stabile mechanical properties to the hydrogel polymer through chain entanglement.

Entanglement is a function of molecular weight, morphology and the charge state of various regions on the polymer. The overall hydrophobicity of the polymer also plays a biologic role since association of water with the polymer matrix contributes to mobility of the constituent polymeric components.

One should note that since the biofunctional groups anticipated here are typically hydrophobic, that inclusion of them on the terminal sites of these molecules contribute significantly to the overall mechanical stability of the polymer.

Biodegradable Hydrophobic Polymers

Polymers can be both hydrophobic and degradable, but exclusion of water generally results in a slower degradation rate. Suitable hydrophobic biodegradable polymeric units include hydroxy acids or other biologically degradable polymers that yield degradation products that are non-toxic or present as normal metabolites in the body.

Hydrophobic biodegradable polymeric structures include polyamino acids, polyanhydrides, polyorthoesters, and polyphosphoesters. Polylactones such as polyepsilon-caprolactone, polydelta-valerolactone, polygamma-butyrolactone and polybeta-hydroxybutyrate, for example, are also useful. Preferred polyhydroxy acids are polyglycolic acid, poly DL-lactic acid and poly L-lactic acid, or copolymers of polyglycolic acid and polylactic acid.

In general, these materials degrade in vivo by both non-enzymatic and enzymatic hydrolysis, and by surface or bulk erosion. Any chemical constituents using linkages susceptible to biodegradation is useful in the present invention, and in particular, linkages formed from ester, peptide, anhydride, orthoester and phosphoester bond.

Non Biodegradable Hydrophobic Polymers

The preponderance of hydrophobic polymers are non-biodegradable, or at least resist degradation over intervals of months or years. Nevertheless, these structures are useful in the present invention since they can be used in conjunction with hydrolyzable blocks. These non-biodegradable hydrophobic polymers or polymeric monomers include polyalkylenes such as polyethylene and polypropylene, polychloroprene, polyvinyl ethers, polyvinyl esters such as polyvinyl acetate, polyvinyl halides such as polyvinyl chloride, polysiloxanes, polystyrene, polyurethanes and copolymers thereof, Hydrophobic moieties with high mechanical strength properties include polyacrylates, such as polymethyl (meth) acrylate, polyethyl (meth)acrylate, polybutyl (meth)acrylate, polyisobutyl (meth)acrylate, polyhexyl (meth)acrylate, polyisodecyl (meth)acrylate, polylauryl (meth)acrylate, polyphenyl (meth)acrylate, polymethyl acrylate, polyisopropyl acrylate, polyisobutyl acrylate, and polyoctadecyl acrylate. To these it is often useful to create polymers comprised of additions of chemical groups, for example, alkyl groups, alkylene groups, hydroxylations, oxidations, and other modifications routinely made by those skilled in the art. Other non-biodegradable polymers include ethylene vinyl acetate, polyacrylates, polychloroprene, and copolymers and mixtures thereof Hydrophilic Side Chains The side chains are preferably hydrophilic, to modify the typically hydrophobic aspect of biofunctional molecules of the present invention. In particular, polycyclic molecules extracted from *Boswellia* or their synthetic analogs. Hydrophilic modification of biofunctional constituents affords greater association with biological constituents, such as cells, and in the case of degradation affords ready transport into tissue structures. For example, it may be desirable to construct a polymer with a first function to block tissue adhesions and a second function, subsequent to degradation, of promoting tissue healing and angiogenesis.

The side chains are preferably water-soluble when not attached to the backbone. Suitable polymeric blocks include those prepared from polyoxyethylene, polyoxypropylene, partially or fully hydrolyzed polyvinyl alcohol, polyvinylpyrrolidone, and dextran. Preferably, the side chains are made from polyoxyethylene, polyoxypropylene, or polyacrylic acids.

Polyoxypropylene is generally not consider hydrophilic, but when copolymerized with polyoxyethylene in a ratio greater than 70:30, polyoxyethylene to polyoxypropylene, the resulting copolymer readily forms stabile hydrogels.

The function of the side chains is not necessarily to impart degradability to the overall polymeric structure, thus the hydrophilic side chains may be intrinsically biodegradable or may be poorly biodegradable or effectively non-biodegradable in the body. In the latter two cases, the side chains should be of sufficiently low molecular weight to allow excretion.

When double-bond containing monomers are used to prepare the polymer backbone, a preferred method for incorporating the hydrophilic side chains is to use a hydrophilic macromonomer with a reactive double bond at one end, which can be randomly incorporated during free radical or other addition polymerization. An example of such a macromonomer is PEG-methacrylate. The density of the hydrophilic side chains along the polymer backbone can be controlled by adjusting the relative amounts of the PEG-methacrylate or other suitable macromonomeric units.

It should be noted that in order for the biofunctional groups to be included one requires appropriate functional groups terminating the side chains, such as —NH.sub.2, —OH, or COOH, on the ends of the macromonomers.

Monomers with Reactive Functional Groups

In many of the embodiments described herein, the monomers used to form the polymer backbone include only two reactive groups, hydroxyl and isocyanate, both of which are reacted in order to form the polymer. For example, lactic acid includes two reactive groups, a hydroxy group and a carboxy group. —OH is the preferred reactive group. Although the ends of a polylactic acid polymer include a hydroxy group and a carboxyl group, there are no reactive groups along the backbone in the final polymer chain that can be used to form a comb copolymer. Therefore, a branching moiety must be incorporated.

Monomers which contain one or more additional reactive groups need to be incorporated into the polymer backbone, preferably in a random fashion, in order to form the comb-type copolymers when monomers that do not include these reactive groups are used to prepare the polymer backbone. Examples of these types of monomers are well known to those of skill in the art.

For example, when lactide is being polymerized using a Lewis acid catalyst, a cyclic dimer of an amino acid can be prepared from lysine, in which the epsilon amine group is protected, for example, with a t-boc protecting group. The lysine is incorporated into the polymer, and the protecting group can be removed. The resulting amine groups are reactive with hydrophilic polymers which include leaving groups such as tosylates, tresylates, mesylates, triflates and other leaving groups well known to those of skill in the art. Additionally, diamine groups such a biocompatible lysine can be used at polymerizing links in isocyanate functionalized polymeric backbones, side chains, and biofunctional end groups.

Alternatively, the reactive monomer can include a leaving group that can be displaced with a nucleophilic group on a hydrophilic polymer. For example, epichlorohydrin can be used during the polymerization step. An example of a suitable hydrophilic polymer containing a nucleophilic group is a polyethylene glycol with a terminal amine group.

PEG-NH.sub.2 can react with the chloride groups on the polymer backbone to provide a desired density of PEGylation on the polymer backbone. Pegylation, in general, is suitable to the botanical extracts of the present invention, since many of them are poorly incorporated in biological tissue, and can be toxic in the absence of hydrophilic modification.

Using the chemistry described herein, along with the general knowledge of those of skill in the art, one can prepare polymer backbones which include suitable leaving groups or nucleophiles for subsequent coupling reactions with suitably functionalized hydrophilic polymers.

Ligands and Linking Groups Coupled to Biofunctional End Groups

Although the principle interest of the present invention is the attachment of biofunctional moieties derived from genus *Boswellia* to hydrogel structures, other botanical extracts are contemplated. Useful botanicals include, camphenes, camphor, coneole and eucal (derived from *eucalyptus*), moronic acid (derived from pistachio), and like structures.

In particular, polycyclic structures with an odd number of cycles is useful in the present invention. More particularly, chiral polycyclic structures of 3 or 5 rings are of interest. The 5-cyclic structures include, @-Boswellic acid, 3-O-Acetyl-β-boswellic acid, 11-Keto-β-boswellic acid, 3-O-Acetyl-11-keto-β-boswellic acid, 11-Hydroxy-β-boswellic acid, 3-O-Acetoxy-11-methoxy-β-boswellic acid, 3-O-Acetyl-11-hydroxy-β-boswellic acid, 9,11-Dehydro-β-boswellic acid, 3-O-Acetyl-9,11-dehydro-β-boswellic acid, α-Boswellic acid, 3-O-Acetyl-α-boswellic acid, Oleanolic acid, Ursolic acid, Baurenol, Lupeol, 11-Hydroxy-α-boswellic acid, 9,11-Dehydro-α-boswellic acid, 3-O-Acetyl-9,11-dehydro-α-boswellic acid, 3-Hydroxy-8,9,24,25-tetradehydro-tirucallic acid, 3-O-Acetyl-8,9,24,25-tetradehydro-tirucallic acid, and 3-Oxo-8,9,24,25-tetradehydro-tirucallic acid.

Ratio of Hydrophilic to Hydrophobic Units

The density of the hydrophilic side chains along the polymer backbone depends in part on the molecular weight of the side chains. The total percent of the hydrophilic units to the hydrophobic units in the present polymers is between 10 and 50 percent by weight, preferably around 30 percent by weight.

The relevant consideration when determining an appropriate ratio of hydrophilic to hydrophobic units is that the overall polymer, when the hydrophilic side chains are not end-capped with cell-signaling moieties, has some non-cell binding properties and preferably incorporates a halo of water around the polymeric construct when implanted. A relatively high density of 500 Dalton or less hydrophilic side chains can provide the same degree of resistance to cellular adhesion as a lower density of higher molecular weight side chains. Those of skill in the art can adjust the molecular weight and density of the polymers taking these factors into consideration.

Density of Tethered Biofunctional Groups

The side chains of the present invention are to be endcapped with cell-signaling chemical ligands in order to elicit specific cell responses. Ligands such as adhesion peptides or growth factors can be covalently or ionically attached to the ends of the side chains using known chemistries to provide specific chemical signals to cells. A defined fraction of ligand-bearing side chains can be obtained by using appropriate stoichiometric control during the coupling of the ligands to the ends of the side chains, by protecting the end-groups on those side chains which are not to be endcapped with ligands, or by combinations of these approaches.

Mixtures of Comb and Dendritic Polymers

When hyaluronan is coupled to a comb or dendritic polymer morphology, cells attach and spread readily on the polymer surface. Preferably, this cellular proliferation is delayed, typically by about 14 days post-implant, so as not to promote tissue adhesion. Thus, there is a need for a first time interval wherein affected tissue surfaces are physically separated, disrupting the usual cellular communications. Thus one purpose of the present disclosure is to initially block such signaling and provide a biofunctional aspect that is released in delayed fashion or encountered only subsequently by infiltrating tissue, to promote the healing response. An important aspect in healing is angiogenesis which provides the metabolic capacity for repair.

With respect to this second phase, the degree of cell spreading and proliferation on the surface of the polymeric implant or the release of constituents that induce such a response within the surrounding tissue can be controlled by mixing adhesion *boswellia* endcapped comb copolymers with strongly hydrophilic dendritic or comb polymer.

The size of the biofunctional clusters, or in other words the spatial area in which the biofunctional groups are localized, is dictated by the characteristic size of the side chains, and can be approximated from the polymer's radius of gyration which can be calculated or experimentally determined by the skilled artisan.

Mixtures of Comb and Dendritic Polymers with Other Polymers

The copolymers described herein can be blended with other polymers that do not elicit controlled cell responses. In applications where it is desirable to use a biofunctionalized copolymer to modify the surface of a second, hydrophobic typical implanted device, the present polymer can be added in small quantities to a second polymer and processed to achieve segregation of bioactive moieties.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein.

As used herein, the term "about" should be construed to refer to both of the numbers specified in any range. Any reference to a range should be considered as providing support for any subset within that range.

Examples are provided to illustrate some embodiments of the embodiments of the present disclosure but should not be interpreted as any limitation thereon. Other embodiments within the scope of the claims herein will be apparent to one skilled in the art from the consideration of the specification or practice of the embodiments or methods disclosed herein. It is intended that the specification, together with the example, be considered to be exemplary only, with the scope and spirit of the disclosure being indicated by the claims which follow the example.

EXAMPLES

The constituents of the following examples are available from Sigma-Aldrich, unless otherwise indicated. In some cases equivalent weights are used rather than gram amounts. When equivalent weights are used, the equivalent is defined with respect to a functional group, for example hydroxyl groups, isocyanate groups, amine groups and the like. The relevant functional group should be obvious to one skilled in the art of the synthesis of polymeric gels. When the word "equivalent" is used, it is meant equivalent weight.

Example 1: Alginate Based Healing Hydrogel

One equivalent of alginate LF 10/60 is reacted with 2 equivalents of toluene diisocyanate at 60 degrees C. until all hydroxyl groups are consumed. One tenth equivalent of glycerol is added to the above synthesis and reacted at 75 degrees C. until all hydroxyl groups are consumed. One tenth equivalent of biofunctional molecule, for example a *boswellia* extract, is added to the above synthesis and reacted at 75 degrees C. until all hydroxyl groups are consumed.

A hydrogel of desired viscosity is formed by adding appropriate amounts of water. For example, for high viscosity gel 1 g water is added, for a low viscosity gel 100 g of water is added. To obtain a gel that changes viscosity in vivo, calcium citrate tetrahydrate can be added to the water component, or added after gel formation to obtain gels with higher viscosity.

Example 2: Poloxamer and Polylactic Acid Based Healing Hydrogel

Pluronic 31R1 (molecular weight 3250) (BASF, Mt. Olive, N.J.) was dried under vacuum at 85.degree. C. for 12 hr. in a spherical flask, the final water content obtained was below 300 ppm. One equivalent of Pluronic 31R1 was added to ⅕ equivalent (l)-Lactide and 0.18 grams catalyst (stannous 2-ethyl hexanoate) (0.43%). The reaction was carried out in a sealed flask, under a dry nitrogen saturated atmosphere, for two and half hours at 145 degrees C.

To the above synthesis is added 2 equivalents of toluene diisocyanate and reacted at 60 degrees C. for 8 hours. To this result is added ½ equivalent of biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added.

Example 3: Polyethylene Glycol and Polylactic Acid Base Healing Hydrogel

Polyethylene glycol (molecular weight 3000) was dried in vacuo overnight at 85.degree. C. Thereafter, the PEG was cooled down to room temperature, and the product capped with dry nitrogen. One equivalent of PEG was added to ⅕ equivalent (1)-Lactide and 0.18 grams catalyst (stannous 2-ethyl hexanoate). The mixture of PEG and lactide is placed in an oil bath under flowing nitrogen at 140.degree. C. and mixed for 3 hours. To the above synthesis is added 2 equivalents of toluene diisocyanate and reacted at 60 degrees C. for 8 hours. To this result is added ½ equivalent of biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added.

Example 4: Poloxamer and Polylactic Acid Based Healing Hydrogel

In a reactor equipped with stir rod, place 2 moles of diisocyanate under nitrogen. Heat the volume to 60.degree. C. and slowly add 1 mole of poloxamer diol. The poloxamer should be added at a rate slow enough such that the volume temperature does not rise above 65.degree. C. If the poloxamer is a solid at 60.degree. C., then a solvent can be used. When all the poloxamer has been added to the reaction volume the mixture should be reacted until the isocyanate content corresponds to two available NCO groups per poloxamer molecule. Adding the poloxamer slowly ensures each poloxamer molecule is endcapped with two diisocyanate molecules, because the majority of the reaction is done in an excess of diisocyanate, and chain extension of the poloxamer is less probable. If prevention of chain extension is important a large excess of diisocyanate can be employed, and the excess diisocyanate evaporated at the termination of the reaction. Once the poloxamer diisocyanate is prepared as described above, 1 mole can be loaded into a reactor under nitrogen, heated to 85.degree. C. and two moles of dilactide (A) or more generally an ester added slowly, and preventing an excessive exotherm. To this result is added ½ equivalent of biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added.

Example 5: Poloxamer and Polylactic Acid Based Healing Hydrogel

While poloxamers of many varied combinations of ethylene oxide (B) and propylene oxide (C) are commercially available, there are practical limits on constructing these chains with monomeric ethylene oxide and propylene oxide. Greater control is afforded by starting with diisocyanates (D) of the monomers, for example DBD or DCD. To these B or C can be arbitrarily added in any combination by forming urethane links between the addition monomer and the diisocyanate end capped chain. Through a step-wise sequence of chain extensions with monomers and subsequent end capping with diisocyanate and combination of B and C can be obtained.

Multi-armed polymers can be constructed without cross-linking by introducing a triol (T) and linking the triol to poloxamer chains with diisocyanate. For example, poloxamer chains are introduced into a reactor and endcapped with diisocyanate. The resulting poloxamer diisocyanate is then reacted with a low molecular weight triol such a trimethylolpropane. The result is a poloxamer triisocyanate which then can be reacted with ester (A). Preferably, the ester is polylactic acid. For every mole of above prepolymer is added ⅒ mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added.

Example 6: Absorbable Polyurethane Based Healing Hydrogel

In a 3-neck flask are placed 400 g of a PLA-Diol (Mn=1000) and 200 g of Terathane 2000 (Invista, Wichita, Kans.). Toluene is added in excess, and the mixture gently heated to remove toluene to obtain a 20% w/w solution. After cooling to room temperature, 650 g of isophorone diisocyanate was added and mixed under dry nitrogen. To the mixture was then added 5 g of dibutyltin-dilaurate (DBTL) and the mixture was heated to 75.degree. C. After 5 hours, 128.7 g of 1,4-butane diol is added and the reaction mixture is diluted with toluene to get concentration of all components of approximately 15% Subsequently, the temperature is raised to 80.degree. C. After 10 hours the mixture is allowed to cool to room temperature. For every mole of above prepolymer is added 1/10 mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 7: Absorbable Polyurethane Based Healing Hydrogel

In a 3-neck flask are placed 400 g of a PLA-Diol (Mn=1000) and 400 g of polyethylene glycol (Mn=2000). Toluene is added in excess, and the mixture gently heated to remove toluene to obtain a 20% w/w solution. After cooling to room temperature, 650 g of isophorone diisocyanate was added and mixed under dry nitrogen. To the mixture was then added 5 g of dibutyltin-dilaurate (DBTL) and the mixture was heated to 75 degrees C. After 5 hours, 128.5 g of 1,4-butane diol is added and the reaction mixture is diluted with toluene to get concentration of all components of approximately 15% Subsequently, the temperature is raised to 80.degree. C. After 10 hours the mixture is allowed to cool to room temperature. For every mole of above prepolymer is added 1/10 mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 8: Absorbable Polyurethane Based Healing Hydrogel

In a 3-neck flask are placed 400 g of a PLA-Diol (Mn=1000) and 400 g of polyethylene glycol (Mn=2000). Toluene is added in excess, and the mixture gently heated to remove toluene to obtain a 20% w/w solution. After cooling to room temperature, 550 g of isophorone diisocyanate was added and mixed under dry nitrogen. To the mixture was then added 5 g of dibutyltin-dilaurate (DBTL) and the mixture was heated to 75 degrees C. After 5 hours, 108.3 g of 1,4-butane diol is added and the reaction mixture is diluted with toluene to get concentration of all components of approximately 15% Subsequently, the temperature is raised to 80.degree. C. After 10 hours the mixture is allowed to cool to room temperature. For every mole of above prepolymer is added 1/10 mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 9: Absorbable Polyurethane Based Healing Hydrogel

In a 3-neck flask are placed 400 g of a PLA-Diol (Mn=1000) and 500 g of polyethylene glycol (Mn=2000). Toluene is added in excess, and the mixture gently heated to remove toluene to obtain a 20% w/w solution. After cooling to room temperature, 512 g of isophorone diisocyanate was added and mixed under dry nitrogen. To the mixture was then added 7 g of dibutyltin-dilaurate (DBTL) and the mixture was heated to 75 degrees C. After 5 hours, 109.5 g of 1,4-butane diol is added and the reaction mixture is diluted with toluene to get concentration of all components of approximately 15%. Subsequently, the temperature is raised to 80.degree. C. After 10 hours the mixture is allowed to cool to room temperature. For every mole of above prepolymer is added 1/10 mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 10: Absorbable Polyurethane Based Healing Hydrogel

In a 3-neck flask are placed 765 g of a PLA-Diol (Mn=1000) and 765 g of polyethylene glycol (Mn=2000). Toluene is added in excess, and the mixture gently heated to remove toluene to obtain a 20% w/w solution. After cooling to room temperature, 955 g of isophorone diisocyanate was added and mixed under dry nitrogen. To the mixture was then added 8 g of dibutyltin-dilaurate (DBTL) and the mixture was heated to 75.degree. C. After 5 hours, 245 g of 1,4-butane diol is added and the reaction mixture is diluted with toluene to get concentration of all components of approximately 15%. Subsequently, the temperature is raised to 80 degrees C. After 10 hours the mixture is allowed to cool to room temperature. For every mole of above prepolymer is added 1/10 mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 11: Absorbable Polyurethane Based Healing Hydrogel

In a 3-neck flask was placed 2100 g of Terathane 2000. Toluene is added in excess, and the mixture gently heated to remove toluene to obtain a 20% w/w solution. After cooling to room temperature, 814 g of isophorone diisocyanate was added and mixed under dry nitrogen. To the mixture was then added 4 g of dibutyltin-dilaurate (DBTL) and the mixture was heated to 75 degrees C. After 5 hours, 193 g of 1,4-butane diol is added and the reaction mixture is diluted with toluene to get concentration of all components of approximately 15%. Subsequently, the temperature is raised to 80 degrees C. After 10 hours the mixture is allowed to cool to room temperature. For every mole of above prepolymer is added ⅒ mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 12: Absorbable Polyurethane Based Healing Hydrogel

In a 3-neck flask was placed 400 g of a PLA-Diol (Mn=2000), 200 g of Terathane 2000 and 200 g of polyethylene glycol (Mn=2000). Toluene is added in excess, and the mixture gently heated to remove toluene to obtain a 20% w/w solution. After cooling to room temperature, 505 g of isophorone diisocyanate was added and mixed under dry nitrogen. To the mixture was then added 7 g of dibutyltin-dilaurate (DBTL) and the mixture was heated to 75 degrees C. After 5 hours, 128.5 g of 1,4-butane diol is added and the reaction mixture is diluted with toluene to get concentration of all components of approximately 15%. Subsequently, the temperature is raised to 80 degrees C. After 10 hours the mixture is allowed to cool to room temperature. For every mole of above prepolymer is added ⅒ mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 13: Absorbable Polyurethane Base Healing Hydrogel

In a 3-neck flask was placed 200 g of a PLA-Diol (Mn=2000), 200 g of polycaprolactone (Mn=2000) and 400 g of polyethylene glycol (Mn=2000). Toluene is added in excess, and the mixture gently heated to remove toluene to obtain a 20% w/w solution. After cooling to room temperature, 505 g of isophorone diisocyanate was added and mixed under dry nitrogen. To the mixture was then added 7 g of dibutyltin-dilaurate (DBTL) and the mixture was heated to 75 degrees C. After 5 hours, 128.5 g of 1,4-butane diol is added and the reaction mixture is diluted with toluene to get concentration of all components of approximately 15%. Subsequently, the temperature is raised to 80 degrees C. After 10 hours the mixture is allowed to cool to room temperature. For every mole of above prepolymer is added ⅒ mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 14: Absorbable Polyurethane Base Healing Hydrogel

Nine hundred grams of Oxymer M112 (carbonate diol, Mn=1500) (Perstorp Specialty Chemicals AB, Perstorp, Sweden) are put into a 3-neck-flask. Toluene is added and partly removed by distillation to get a 20% solution. After cooling to room temperature 96.2 g of hexamethylene diisocyanate are added under nitrogen. 6 g of DBTL are added and the mixture is heated to 75° C. After 5 hours the temperature is raised to 80° C. After 10 hours the mixture is allowed to cool to room temperature. For every mole of above prepolymer is added ⅒ mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 15: Absorbable Polyurethane Based Healing Hydrogel

Six hundred grams of Desmophen 2100 (carbonate diol, Mn=1000) (Bayer, Morristown, N.J.) are put into a 3-neck-flask. Toluene is added and partly removed by distillation to get a 20% solution. After cooling to room temperature 181.3 g of isophorone diisocyanate is added under nitrogen. 6 g of DBTL are added and the mixture is heated to 75° C. After 5 hours the temperature is raised to 80° C. After 10 hours the mixture is allowed to cool to room temperature. For every mole of above prepolymer is added ⅒ mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 16: Absorbable Polyurethane Based Healing Gel

Seven hundred grams of Terathane 2000 (Invista, Wichita, Kans.) are put into a 3-neck-flask. Toluene is added and then a part of the toluene is removed by distillation to get a 20% solution. After cooling to room temperature, 288 g of isophorone diisocyanate are added under nitrogen. 6 g of DBTL are added and the mixture is heated to 75° C. After 5 hours 128.7 g of 1,4-butane diol are added and the reaction mixture is diluted with toluene to get concentration of all components of 15% The temperature is raised to 80° C. After 10 hours the mixture is allowed to cool to room temperature. For every mole of above prepolymer is added ⅒ mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 17: Absorbable Polyurethane Based Healing Hydrogel

Four thousand two hundred grams of Terathane 2000 are put into a 3-neck-flask. Toluene is added and than a part of the toluene is removed by distillation to get a 20% solution. After cooling to room temperature 1514 g of isophorone diisocyanate are added under nitrogen. 7 g of DBTL are added and the mixture is heated to 75° C. After 4 hours 617 g of 1,4-bis(N-methyl)amino cyclohexane are added and the reaction mixture is diluted with toluene to get concentration of all components of 10% The temperature is raised to 80°

C. After 8 hours the mixture is allowed to cool to room temperature. For every mole of above prepolymer is added 1/10 mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 18: Absorbable Polyurethane Based Healing Hydrogel

Four hundred grams of Terathane 2000 and 400 g of polycaprolactone diol (Mn=2000) are put into a 3-neck-flask. Toluene is added and then a part of the toluene is removed by distillation to get a 20% solution. After cooling to room temperature, 505 g of isophorone diisocyanate are added under nitrogen. 7 g of DBTL are added and the mixture is heated to 75° C. After 5 hours 128 g of 1,4-butane diol are added and the reaction mixture is diluted with toluene to get concentration of all components of 15% The temperature is raised to 80° C. After 10 hours the mixture is allowed to cool to room temperature. For every mole of above prepolymer is added 1/10 mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 19: Absorbable Polyurethane Based Healing Hydrogel 476 g of Terathane 2000 and 600 g of polycaprolactone diol (Mn=2000) are put into a 3-neck-flask. Toluene is added and then a part of the toluene is removed by distillation to get a 20% solution. After cooling to room temperature, 404 g of isophorone diisocyanate are added under nitrogen. 4 g of DBTL are added and the mixture is heated to 75° C. After 5 hours 93 g of 1,4-butane diol are added and the reaction mixture is diluted with toluene to get concentration of all components of a 15% The temperature is raised to 80° C. After 10 hours the mixture is allowed to cool to room temperature. For every mole of above prepolymer is added 1/10 mole biofunctional molecule, for example a *boswellia* extract and reacted at 75 degrees C. for 8 hours. A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 20: Substituting a Carbamate Link for a Urea Link

Any of the examples of polymers described thus far can be functionalized by addition of a terminal amine group suitable for attachment of a bioactive substance. One approach is to amine terminate an ether diol and then polymerize this reaction product with an ester.

An amine terminated PEG can be synthesized by dissolving the PEG into dry THF at −79 degree C. utilizing dry ice and methanol as a cooling bath. The amount of amine termination is calculated, and the equivalent amount of 0.25 M solution of potassium-bis-(trimethylsilyl) amide in toluene is then added slowly.

The reaction mixture is then stirred at 20 degree C. for 48 hours. The reaction product is then diluted 10:1 with ether forming a precipitate which can be subsequently separated from solution by filtration. The precipitate is then dissolved in THF and 0.1N hydrochloric acid was added to split the silylamide. The solution is then stirred for 1 hour at room temperature, and then the polymer is precipitated in ether. The resulting $NH_2$-PEG can be polymerized with cyclic DL-dilactide. In the desired ratio, the two ingredients are dissolved separately in dry toluene. The polymerization is accomplished by combining the two solutions under dry nitrogen and heating to boiling. When boil is reached, tin catalyst (tin-2-ethylhexanoate) is then added and reacted for 8 hours. The resulting polymer solution is cooled and mixed with dichloromethane to remove water by evaporation. The dicholoromethane of the dry solution is exchanged with acetone and the resulting solution dripped into distilled water at 0 degree C. and the resulting precipitate collected.

Example 21

Polyethylene oxide/polypropylene oxide backbone for a healing hydrogel. Any of the alcohols used in the above examples may be substituted with polyethylene oxide/polypropylene oxide as synthesized below. Water soluble tri-block copolymers of polyethylene oxide (PEO) and polypropylene oxide (PPO) are commercially available non-ionic macromolecular surface active agents. Variation of the copolymer composition (PPO/PEO ratio) and molecular weight (PEO and PPO block lengths) during synthesis leads to the production of molecules with optimum properties. Unfortunately, commercially available forms employ block structures that are typically larger than are most desired for the present invention.

Since PEO is more reactive than PPO fine scale block structures cannot be formed by merely placing the ratio amounts of PEO and PPO together in a reactor. Alternating segments of PEO and PPO can be synthesized by the sequential addition of first propylene oxide (PO) and then ethylene oxide (EO). These oxyalkylation steps are carried out in the presence of an alkaline catalyst, for example, sodium or potassium hydroxide. The catalyst is then neutralized and removed from the final product. By alternating additions of EO and PO one can make copolymers of particular PPO/PEO composition while varying the molecular weight of the PPO blocks. Thus a complete grid of copolymers are realizable, the grid comprised of constant PPO/PEO composition on the vertical axis and constant PPO block molecular weight on the horizontal axis.

Example 22: Hyaluronan Isocyanate Functional Groups for Synthesizing Healing Hydrogel Any of the isocyanate components in the above may be substituted with the below described hyaluronan Isocyanate.

Hyaluronan is comprised of repeating segments of $C_{14}H_{21}NO_{11}$, each containing 5 hydroxyl groups (OH). To form a diisocyanate of hyaluronan one reacts a quantity of diisocyanate containing 2 moles of NCO greater than the number of moles of OH. Thus, a hyaluronan containing 1 unit of $C_{14}H_{21}NO_{11}$ per molecule, then 1 mole of hyaluronan molecules if to be reacted with 7 moles of diisocyanate. The reaction is performed in an organic solvent, where the hyaluronan is altered by ammonia to make it soluble in an organic solvent, for example tetrahydrofuran. A small amount of tin catalyst is added to promote urethane link formation between the hydroxyls of the hyaluronan and the isocyanate groups of the diisocyanate. To discourage chain extension, the hyaluronan is first dissolved in organic solvent and set aside. The reactor is charged with catalyst and diisocyanate and heated to 80 degrees C. The hyaluronan solution is slowly added to the reactor and the exotherm monitored. Complete reaction is indicated when the exotherm subsides. Alternatively, one can measure the % NCO at each step to verify all the hydroxyl groups on the hyaluronan are endcapped with isocyanate.

When all the hyaluronan is added to the reactor the reaction is run until the desired % NCO is reached. % NCO is measured by conventionally by dibutylamine titration. The reaction is complete when 2 moles of NCO are measured for every mole of product molecule. Ideally there is only 1 $C_{14}H_{21}NO_{11}$ unit per product molecule. However, in other applications a spectrum of product molecules containing a range of $C_{14}H_{21}NO_{11}$ unit per product molecule is desired. The desired polydispersity can be obtained by adjusting the amount of NCO used, and verifying with GPC and % NCO measurements. In any one reaction, the dispersity of molecular weights of product molecules will be Gaussian around a desired mean. Multi-modal distributions can be obtained by mixing the reaction product of multiple reactions.

Hyaluronan isocyanates of higher isocyanate functionality can be synthesized by adjusting the ratio of OH groups to isocyanate groups in the reaction mix.

Example 23: Hyaluronan Polyurethane Based Healing Hydrogel

A polyalkylene copolymer of PPO and PEO is synthesized according to EXAMPLE 21 wherein the PEO blocks contain 3 propylene oxide units, the PPO blocks contain 1 ethylene oxide unit, and these PEO and PPO blocks alternate, wherein the first block is a PEO and the last block is a PPO. The number of functional OH groups per molecule is approximately 2. A hyaluronan diisocyanate is synthesized according to EXAMPLE 22 wherein the molecular weight of the hyaluronan diisocyanate is approximately 3 times the molecular weight of the polyalkylene copolymer. If the polyalkylene component or the hyaluronan diisocyanate components are not in liquid form at a reaction temperature of approximately 80 degrees C., then these components are dissolved in an organic solvent devoid of OH groups. The reactor is charge with 1 mole of hyaluronan diisocyanate and heated to 80 degrees C. The polalkylene copolymer is added slowly, waiting for the exotherm to subside after each addition.

If a prepolymer is desired, a reaction product that will polymerize on a mesh, then the component amounts are chosen to result in 2 moles of NCO per product molecule. Chains of arbitrary length of hyaluronan and polyalkylene can be synthesized by choosing the amount of isocyanate such that 2 moles of NCO remain per desired molecular weight of product molecule.

In some cases, a prepolymers with 3 or higher isocyanate functionality per product molecule is desired, so that when polymerized on a medical device the coating is resistant to solvents or heat. Not every molecule must have higher functionality to obtain a polymerization product that is crosslinked.

If a linear polymer is desired, wherein the reaction product can be dissolved in solvent and solution cast, or melted and extruded, then some of the hyaluronan diisocyanate must be endcapped with a mono-functional alcohol such as ethanol. The molecular weight of the reaction product is selected by the ratio of diisocyanate to mono-isocyanate hyaluronan in the reaction mix.

Alternatively, the chain extension can be terminated in reaction by adding ethanol to the reaction mix when the desired molecular weight is obtained. In this instance an excess of ethanol can be used, which is driven off by evaporation when all the NCO groups are consumed.

Dibutylamine titration can be used to determine when a reaction is done. In particular, in the polymer case, the reaction is complete when all NCO groups are consumed. In the prepolymers case, the reaction is complete when the NCO number per product molecule reaches a desired value. In the case of crosslinking prepolymers the NCO number is greater than 2 per product molecule. In the case of non-crosslinking prepolymers the NCO number equals 2 per product molecule.

The product molecules and polymerized forms are characterized by possessing in number ratio approximately 3 segments of hyaluronan per segment of polyalkylene. The polyalkylene segment comprises in number ratio approximately 3 segments of ethylene oxide per segment of propylene oxide. The hyaluronan segment is more hydrophilic than the polyalkylene segment. The ethylene oxide segment is more hydrophilic than the propylene oxide segment. The urethane links between hyaluronan units having a molecular weight ratio of urethane to hyaluronan approximately the same as the molecular weight ratio of urethane to polyalkylene segments. The urethane links is more hydrophobic than the hyaluronan units or polyalkylene segments. The density of which can be tailored to form hard segment association between urethane links within the bulk volume of the polymer.

For every mole of above prepolymer is added 1/10 mole biofunctional molecule, for example a *boswellia* extract and reacted at 75 degrees C. for 8 hours.

A hydrogel of desired viscosity is formed by adding appropriate amounts of water. For example, for high viscosity gel 1 g water is added, for a low viscosity gel 100 g of water is added. After hydrogel formation, the toluene is driven in an excess of water to obtain a solvent free hydrogel.

Example 24: Preparation of Polyester Diisocyanate Functional Groups for Synthesizing Healing Hydrogel In this example a castor-derived hydroxyl-terminated ricinoleate derivative is used as the diol. One equivalent of polycin D-265 (212 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=10.9%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (424 Dalton+2×174 Dalton) yielding approximately 10.9%.

Alternatively, a lower molecular weight diol may be used, such as polycin D-290 where 1 equivalent of polycin D-290 is 193 g and the target % NCO is 84/(386+348)=11.4%.

Alternatively, a higher molecular weight diol may be used, such as polycin D-140 where 1 equivalent of polycin D-140 is 400 g and the target % NCO is 84/(800+348) =7.3%.

All polycin diols are available from Performance Materials (Greensboro, N.C.) and toluene diisocyanate is available from Sigma-Aldrich (Milwaukee, Wis.).

Example 25: Preparation of Polyether Diisocyanate Functional Groups for Synthesizing Healing Hydrogel In this example a polyether hydroxyl-terminated copolymer of 75% ethylene oxide and 35% propylene oxide is used as the diol. One equivalent of UCON 75-H-450 (490 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=10.9%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (980 Dalton+2×174 Dalton) yielding approximately 6.3%.

Polyether copolymers of ethylene oxide and propylene oxide diols are available from Dow Chemical (Midland, Mich.).

Example 26: Preparation of Polyester Triisocyanate Functional Groups for Synthesizing Healing Hydrogel In this example a castor-derived hydroxyl-terminated ricinoleate derivative is used as the triol. One equivalent of polycin T-400 (141 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=13.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (282 Dalton+2×174 Dalton) yielding approximately 13.3%.

The above reaction will yield a viscous product. A less viscous product can be obtained by adding propylene carbonate to the initial mixture. Additions up to 100% by weight of propylene carbonate are useful. Adjustment to the target NCO of the mixture must be performed using standard methods, or the propylene carbonate may be added after reaching the target % NCO. Propylene carbonate is available from Sigma-Aldrich (Milwaukee, Wis.).

Example 27: Preparation of Polyether Triisocyanate Functional Groups for Synthesizing Healing Hydrogel In this example a polyether hydroxyl-terminated copolymer of 75% ethylene oxide and 35% propylene oxide is used as the triol. One equivalent of Multranol 9199 (3066 g) is combined with 3 equivalent of toluene diisocyanate (261 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=1.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (3×42 Dalton) per product molecule by the total weight of the product molecule (9199 Dalton+3×174 Dalton) yielding approximately 1.3%. Multranol 9199 is available from Bayer (Pittsburgh, Pa.).

Example 28: Preparation of a Polyol Triisocyanate from Polyol Diol Functional Groups for Synthesizing Healing Hydrogel Any of the diisocyanates prepared above can be trimerized by the addition of a low molecular weight triol such as polycin T-400 or trimethylolpropane (TMP). In this example TMP is used, but the method is adaptable to any triol. Complete trimerization of the diisocyanates of Example 1 and 2 will result in viscous products. To yield a lower viscosity product propylene carbonate can be employed or less triol can be used. In the later case, a mixture of diisocyanate and triisocyanate is obtained.

In this example the product of Example 26 is used as the polyether diisocyanate. One equivalent of Example 26 (682 g) is combined with 0.1 equivalent TMP (44.7 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=5.8%. The target % NCO is reached when every hydroxyl group in the mixture is reacted with an NCO group. The ideal % NCO is calculated by dividing the weight fraction of the functional isocyanate groups 10% (3×42 Dalton) and 90% (2×42) per product molecule by the total weight fraction of the product molecule (3×1364 Dalton+ 134 Dalton)+1364 yielding approximately 0.3%+ 5.5%=5.8%. TMP is available from Sigma-Aldrich (Milwaukee, Wis.).

Example 29: Preparation of a Modified *Boswellia* Extract Using a Triisocyanate The hydroxyl number of *Boswellia* extract will vary depending on extraction method, species of *Boswellia* extracted, and even variations within species. The goal is to obtain a product with no NCO functionality, so all reaction mixtures should be reacted until the final % NCO=0.

In this example a triisocyanate is used as the polyether triisocyanate mixture. One hundred grams of Example 28 is combined with 1 g of *Boswellia* extract at room temperature (22° C.) under 90% nitrogen and 10% nitric oxide atmosphere. The mixture is stirred at 100 revolutions per minute and the temperature monitored. When the temperature ceases to rise, a % NCO reading is taken. If % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added to the mixture and the mixture is reacted so that % NCO=0 is obtained.

Example 30: Preparation of Modified *Boswellia* Extract Using a Triisocyanate Preparation of a modified *Boswellia* extract using the triisocyanate/diisocyanate of Example 29. The hydroxyl number of *Boswellia* extract will vary depending on extraction method, species of *Boswellia* extracted, and even variations within species. The goal is to obtain a product with no NCO functionality, so all reaction mixtures should be reacted until the final % NCO=0.

In this example the product of Example 29 is used as the polyether diisocyanate/triisocyanate mixture. One hundred grams of Example 29 is combined with 1 g of *Boswellia* extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added to the mixture and the mixture is reacted so that % NCO=0 is obtained.

Example 31: Preparation of Modified *Boswellia* Extract Using Multi-Branched Isocyanate Diol and triol can be combined to form a multi-branch polymer. In this instance, the Multranol 9199 triol is chain extended with polycin D-265 diol. The diisocyanate form of Example 2 is useful in chain extending the triisocyanate form of Example 28. We wish to have on average 2 diisocyanates for every 3 triisocyanates, which forms a 5 armed isocyanate.

In this example 0.09 equivalents (292 g) of Example 28 is mixed with 0.04 equivalents (26.6 g) of Example 26. The triisocyanates of Example 28 and diisocyanates of Example 26 are chain extended with 0.08 equivalents lysine diamine to form a 5 armed isocyanate. One hundred grams of this reaction product is combined with 1 g of *Boswellia* extract at room temperature (22° C.) under 90% nitrogen and 10% nitric oxide atmosphere. The mixture is stirred at 100 revolutions per minute and the temperature monitored. When the temperature ceases to rise, a % NCO reading is taken. If % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added to the mixture and the mixture is reacted so that % NCO=0 is obtained. Lysine diamine is available from Sigma-Aldrich (Milwaukee, Wis.).

Example 32: Preparation of Modified *Boswellia* Extract Using Multi-Branched Isocyanate A polyether hydroxyl-terminated copolymer of 75% ethylene oxide and 35% propylene oxide is used as the triol. One equivalent of Multranol 9199 (3066 g) is combined with 3 equivalent of toluene diisocyanate (261 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=1.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. The ideal % NCO is calculated by dividing the weight of the functional isocyanate groups (3×42 Dalton) per product molecule by the total weight of the product molecule (9199 Dalton+3×174 Dalton) yielding approximately 1.3%. Multranol 9199 is available from Bayer (Pittsburgh, Pa.).

Example 33: Preparation of a Modified *Boswellia* Extract

The hydroxyl number of *Boswellia* extract will vary depending on extraction method, species of *Boswellia* extracted, and even variations within species. The goal is to obtain a product with no NCO functionality, so all reaction mixtures should be reacted until the final % NCO=0.

One hundred grams of the above triisocyanate is combined with 1 g of *Boswellia* extract at room temperature (22°

C.) under 90% nitrogen and 10% nitric oxide atmosphere. The mixture is stirred at 100 revolutions per minute and the temperature monitored. When the temperature ceases to rise, a % NCO reading is taken. If % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added to the mixture and the mixture is reacted so that % NCO=0 is obtained.

What is claimed is:

1. A copolymeric hydrogel comprising a polymerization product of an anionic polysaccharide, a diisocyanate, and a linker,
   wherein the linker comprises i) an ether group, an ester group, or a combination thereof and, ii) a chain extender comprising a hydroxyl group, a thiol group, an amine group, or a combination thereof,
   and wherein the copolymeric hydrogel comprises at least 30% by weight of water bound to the hydrogel by hydrogen bonding.

2. The copolymeric hydrogel of claim 1, wherein the polymerization product comprises a copolymer of a prepolymer and the linker, wherein:
   the prepolymer comprises a copolymer of the anionic polysaccharide and the diisocyanate.

3. The copolymeric hydrogel of claim 1, wherein the prepolymer comprises at least one segment represented by I[UPUUPU]sI, wherein, independently for each occurrence, P represents a polysaccharide block, U represents a urethane or urea block, I represents an isocyanate and s represents and integer ranging from 1 to 10,000.

4. The copolymeric hydrogel of claim 1, wherein the linker comprises at least one segment represented by EGE, wherein, independently for each occurrence, G represents an ether block, an ester block or a combination thereof, and E represents a chain extender comprising a hydroxyl, a thiol or an amine group.

5. The copolymeric hydrogel of claim 1, wherein the polymerization product comprises at least one segment represented by I[UPUUPU]nUGU[UPUUPU]nI, wherein, independently for each occurrence, P represents a polysaccharide block, U represents a urea or urethane block, G represents an ether block, an ester block or a combination thereof, and s represents an integer ranging from 1 to 10,000.

6. The copolymeric hydrogel of claim 5, further comprising at least one biofunctional molecule.

7. The copolymeric hydrogel of claim 5, further comprising at least one biofunctional molecule.

\* \* \* \* \*